United States Patent [19]
Ruben et al.

[11] Patent Number: 5,641,657
[45] Date of Patent: Jun. 24, 1997

[54] DNA ENCODING AN INTERLEUKIN-6 SPLICE VARIANT

[75] Inventors: Steven Ruben, Olney; Haodong Li, Germantown; Mark D. Adams, Potomac, all of Md.

[73] Assignee: Human Genome Sciences, Inc., Rockville, Md.

[21] Appl. No.: 246,427

[22] Filed: May 19, 1994

[51] Int. Cl.$^6$ ............................ C12N 15/24; C07K 14/54
[52] U.S. Cl. ........................ 435/69.52; 435/252.3; 435/320.1; 435/325; 435/365.1; 435/358; 435/419; 435/348; 536/23.5; 530/351
[58] Field of Search .......................... 435/69.52, 243, 435/240.2, 252.3, 320.1; 514/2, 44; 530/351; 536/23.1, 23.5

[56] References Cited

FOREIGN PATENT DOCUMENTS 2080504  10/1992  Canada.
WO8800206  1/1988  WIPO.
WO9301212  1/1993  WIPO.

OTHER PUBLICATIONS

Yasukawa et al (1987) The EMBO Journal, 6:2939–2945.
Haegeman et al (1986) Eur. J. Biochem 159:625–632.
Hivano et al (1986) Nature 324:73–76.
Zilberstein et al (1986) The EMBO Journal 5:2529–2537.

Primary Examiner—John Ulm
Assistant Examiner—Prema Mertz
Attorney, Agent, or Firm—Elliot M. Olstein; Charles J. Herron

[57] ABSTRACT

Polynucleotides which encode the polypeptide IL-6SV, as well as such polypeptides, antibodies and antagonist inhibitors against the polypeptide and the use of the polypeptide as a pharmaceutical for treating cancer, auto-immune diseases, platelet reducing conditions, anemias, bone marrow and organ transplantation.

32 Claims, 4 Drawing Sheets

FIG. 1A

```
                                                  .
                                    GCCCCAGTACCCCAGGAGAAGAT
                                    -----------+-----------       104
                                    CGGGGTCATGGGGTCCTCTTCTA
                                              A  P  V  P  P  G  E  D
81

.                    .                    .
TCCAAAGATGTAGCGGCCCCACACAGACAGCCACTCACCTCTTCAGAACGAATTGACAAA
-----------+-----------+-----------+-----------+-----------+   164
AGGTTTCTACATCGCCGGGGTGTGTCTGTCGGTGAGTGGAGAAGTCTTGCTTAACTGTTT
 S  K  D  V  A  A  P  H  R  Q  P  L  T  S  S  E  R  I  D  K
105

.                    .                    .
CAAATTCGGTACATCCTGACGGCATTCAGCCCTGAGAAAGAGACATGTAACAAGAGT
-----------+-----------+-----------+-----------+-----------+   224
GTTTAAGCCATGTAGGACTGCCGTAAGTCGGGACTCTTTCTCTGTACATTGTTCTCA
 Q  I  R  Y  I  L  D  G  I  S  A  L  R  K  E  T  C  N  K  S
165

.                    .                    .
AACATGTGTGAAAAAGATGGATGCTTCCAATCTGGATTCAATGAGGAGACTTGCCTGGTG
-----------+-----------+-----------+-----------+-----------+   284
TTGTACACACTTTTTCTACCTACGAAGGTTAGACCTAAGTTACTCCTCTGAACGGACCAC
 N  M  C  E  K  D  G  C  F  Q  S  G  F  N  E  E  T  C  L  V
225

.                    .                    .
AAAATCATCACTGGTCTTTTGGAGTTTGAGGTTTATACCTAGAGTACCTCCAGAACAGATTT
-----------+-----------+-----------+-----------+-----------+   344
TTTTAGTAGTGACCAGAAAACCTCAAACTCCATATATGGATCTCATGGAGGTCTTGTCTAAA
 K  I  T  G  L  L  E  F  E  V  Y  L  E  Y  L  Q  N  R  F
285
```

FIG. 1B

```
345  CTCTCATCACTCCTTGTTCTTGCGTCCAGACGTCTACTCATGTTTCAGGACTAGGTCAAG    404
     GAGAGTAGTGAGGAACAAGCCAGACGTGTCAGATGAGTACAAAAGTCCTGATCCAGTTC
      E  S  S  E  E  Q  A  R  A  V  Q  M  S  T  K  V  L  I  Q  F

405  CTGCAGAAAAAGCAAAGCTAGATGCAATAACCACCCCTGACCAACCACAAATGCC           464
     GACGTCTTTTTCGTTTCGATCTACGTTATTGTGGGGACTGGTTGGTGTTACG
      L  Q  K  K  A  K  N  L  D  A  I  T  T  P  D  P  T  T  N  A

465  AGCCTGCTGACGAAGCTGACAGAACCAGTGGCTGCAGGACGTCAGGACATGACAACTCATCTC    524
     TCGGACGACTGCTTCGACTGTCTTGGTCACCGACGTCCTGCAGTCCTGTACTGTTGAGTAGAG
      S  L  L  T  K  L  Q  A  Q  N  Q  W  L  Q  D  M  T  T  H  L

525  ATTCTGCGCAGTTTAAGGAGTTCCTGCAGTCCAGCCTTGAGGCTCTTCGGCAAATGTAG      584
     TAAGACGCGTCAAATTCCTCAAGGACGTCAGGTCGGAACTCCGAGAAGCCGTTTACATC
      I  L  R  S  F  K  E  F  L  Q  S  S  L  R  A  L  R  Q  M  *

585  CAT      587
     GTA
```

FIG. 2

```
                                  27 APVPPGEDSKDVAAPHRQPLTSS 50
                                     ||||||||||||||||||||||||
                                  27 APVPPGEDSKDVAAPHRQPLTSS 50

51 ERIDKQIRYILDGISALRKETCNKSNMC.................EKDG 82
    ||||||||||||||||||||||||||||                 ||||
 51 ERIDKQIRYILDGISALRKETCNKSNMCESSKEALAENNLNLPKMAEKDG 100

83 CFQSGFNEETCLVKIITGLLEFEVYLEYLQNRFESSEEQARAVQMSTKVL 132
    ||||||||||||||||||||||||||||||||||||||||||||||||||
101 CFQSGFNEETCLVKIITGLLEFEVYLEYLQNRFESSEEQARAVQMSTKVL 150

133 IQFLQKKAKNLDAITTPDPTTNASLLTKLQAQNQWLQDMTTHLILRSFKE 182
    ||||||||||||||||||||||||||||||||||||||||||||||||||
151 IQFLQKKAKNLDAITTPDPTTNASLLTKLQAQNQWLQDMTTHLILRSFKE 200

183 FLQSSLRALRQM 194
    ||||||||||||
201 FLQSSLRALRQM 212
```

DNA ENCODING AN INTERLEUKIN-6 SPLICE VARIANT

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Interleukin-6 splice variant (IL-6SV). The invention also relates to inhibiting the action of such polypeptides.

Interleukin-6 is a multifunctional cytokine produced and secreted by several different cell types. This cytokine plays a central role in cell defense mechanisms including the immune response, acute phase response and hematopoiesis. Interleukin-6 (IL-6) is a 20 to 26 kDa phosphoglycoprotein that has been cloned previously (May et al, Proc Natl Acad Sci USA 83:8957 (1986)); Zilberstein et al, EMBO J 5:2529 (1986); Hirano et al, 1986 Nature (London) 234–73 (1986)). IL-6 has previously been referred to as B cell stimulatory factor 2 (BSF-2), interferon-beta 2 (INF-β2) and hepatocyte stimulating factor. IL-6 is secreted by a number of different tissues including the liver, spleen, and bone marrow and by a variety of cell types including monocytes, fibroblasts, endothelial cells, B-cells and T-cells.

IL-6 is activated at the transcriptional level by a variety of signals including viruses, double stranded RNA, bacteria and bacterial lipopolysaccarides, and inflammatory cytokines such as IL-1 and TNF. This protein is multi-functional growth factor acting on numerous cell types. IL-6 transcriptionally activates a set of the acute phase proteins in hepatocyte cultures. When immortalized B lymphocytes are treated with IL-6, it acts as a growth factor and stimulates immunoglobulin production. IL-6 also acts as a T cell accessory signal and induces cytotoxic T cells.

Based on its ability to induce cellular differentiation, IL-6 has been shown to inhibit growth in several leukemia/ lymphoma cell lines, in neuronal cells and in fibroblasts (Chen et al, Proc Nat'l Acad Sci USA 85:8037 (1988)). B-cell neoplasms are a heterogeneous group of diseases characterized by different maturation states of the B-cell, which are related to the aggressiveness of the disorder. Chronic lymphocytic leukemia (CLL) is characterized by proliferation and accumulation of B-lymphocytic leukemia (BLL) is characterized by proliferation and accumulation of B-lymphocytes that appear morphologically mature but are biologically immature. This disorder accounts for 30% of leukemias in Western countries. The disorder is characterized by proliferation of biologically immature lymphocytes, unable to produce immunoglobulins, which cause lymph node enlargement. Whereas it would be expected that IL-6 would promote the growth of leukemic B-cells from CLL patients, IL-6 inhibits proliferation of these cells.

In addition, IL-6 acts synergistically with IL-3 to enhance both IL-3 dependent colony formation of multi-potential hemopoietic progenitor cells and differentiation of macrophage/neutrophil bone marrow colonies.

IL-6 is an important mediator in vivo to a number of insults including bacterial LPS, severe burns, and sepsis. In animals with tumors, elevated levels of circulating IL-6 have been detected. In addition, increased levels of IL-6 have been shown in cancer patients treated with TNF or IL-2.

PCT Application No. WO 88/00206 discloses IL-6 which is produced by a recombinant DNA techniques. The IL-6 peptide is useful in the treatment of disorders characterized by deficiencies in hematopoietic cells and in combination with other hematopoietins in cancer therapies.

Canadian Patent Application No. 2080504 relates to the use of IL-6 in the manufacture of a pharmaceutical composition for the treatment of CLL or B-cell lymphomas.

PCT Application No. WO 93/01212 discloses muteins of IL-6 and truncated IL-6 which are prepared by recombinant DNA techniques. In the muteins, the cysteine residues that occur at positions, or at positions corresponding to positions 45 and 51 of mature, native IL-6 have been replaced by other amino acids. The cysteine residues that occur at positions, or at positions corresponding to position 74 and 84, are retained. The molecule has biological activity that is at least comparable to that of native IL-6.

The present invention is directed to a splice variant of IL-6 having biological activity at least comparable to that of native IL-6.

In accordance with one aspect of the present invention, there is provided a novel mature polypeptide which is IL-6SV, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there is provided a process for utilizing such polypeptide, or polynucleotide encoding such polypeptide for therapeutic purposes, for example, as anti-tumor agent, to treat immunodeficiency diseases, to treat platelet reducing conditions, shock syndromes, as an anti-viral agent, to inhibit proliferation of leukemic cells, to improve the toxic activity of human lymphocytes for killing cancer cells, for use in cell transplant therapy, and inflammation.

In accordance with yet a further aspect of the present invention, there is provided an antibody against such polypeptides.

In accordance with yet another aspect of the present invention, there are provided antagonist/inhibitors to such polypeptides, which may be used to inhibit the action of such polypeptides, for example, in the treatment of autoimmune, immuno-inflammatory, neoplastic and infectious diseases including multiple myeloma and Kaposi's sarcoma.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE DRAWINGS

FIG. 1 discloses the cDNA sequence and corresponding deduced amino acid sequence encoding for the mature IL-6SV polypeptide. The standard one letter abbreviation for amino acids is used throughout.

FIG. 2 compares IL-6SV with IL-6 at the amino acid level. The top line is IL-6SV and the bottom line is IL-6.

DESCRIPTION OF THE INVENTION

Figure 3:
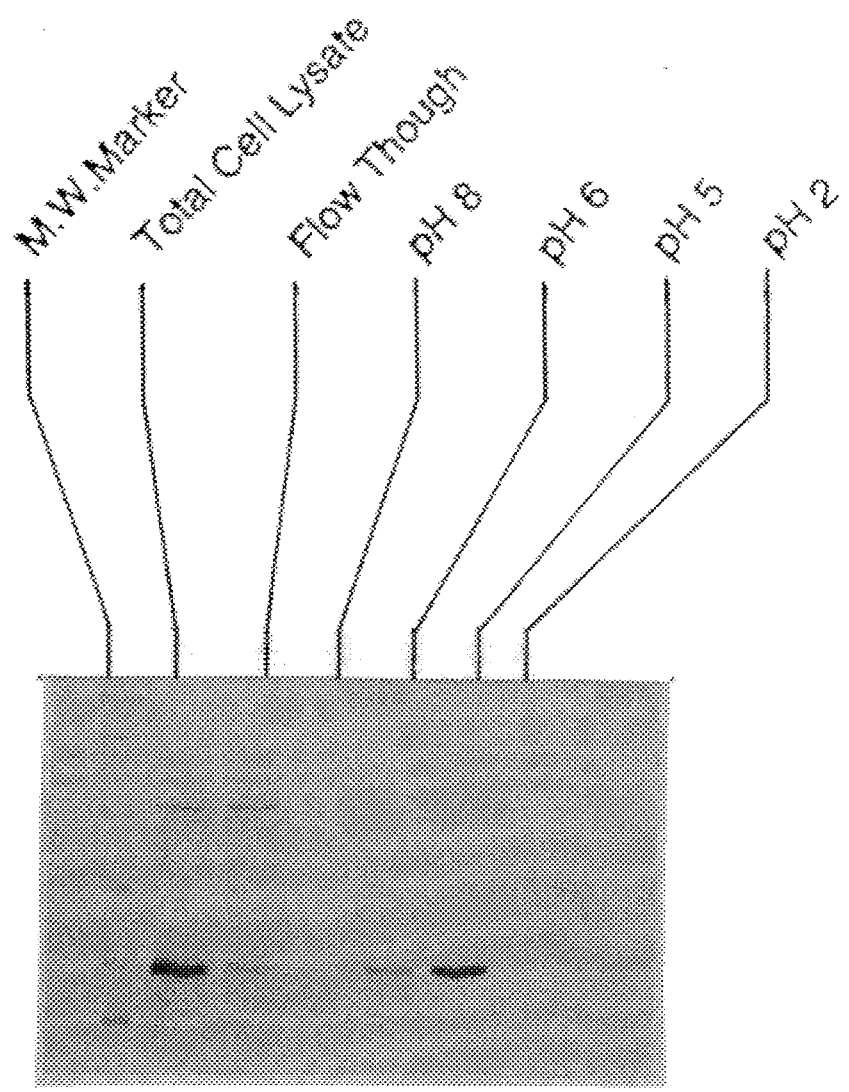
FIG. 3 depicts the results of electrophoresing IL-6SV on a gel after bacterial expression and purification.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC (American Type Culture Collection, 12301 Parklawn Drive, Rockville, Md. 20852 USA) Deposit No. 75697 on Mar. 4, 1994.

The polynucleotide of the present invention was isolated from an activated macrophage cDNA library. It contains an open reading frame encoding a polypeptide of 168 amino acids. The polypeptide is identical to IL-6 except for an 18 amino acid deletion within the open reading frame (see FIG. 2) (SEQ ID NO. 2 and 5).

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO: 1) or that of the deposited clone or may be a different coding sequence which coding sequence, as a result of the redundancy or degeneracy of the genetic code, encodes the same mature polypeptide as the DNA of FIG. 1 (SEQ ID NO: 1) or the deposited cDNA.

The polynucleotide which encodes for the mature polypeptide of FIG. 1 (SEQ ID NO: 2) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide. For example, the first 80 nucleotides of the IL-6SV polypeptide (not shown) encode for amino acids which represent the signal peptide which is cleaved to form the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO: 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode for a fragment, derivative or analog of the polypeptide of FIG. 1 (SEQ ID NO: 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO: 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a IL-6SV polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the IL-6SV genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis, USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification. (Price et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

IL-6SV may be used to activate mature lymphoid cells, which have cytolytic activity. IL-6SV may, therefore, be used therapeutically as anticancer and antiviral treatments.

IL-6SV may be used to treat metastatic cancers. IL-6SV improves the toxic activity of human lymphocytes for killing cancer cells. Along these same lines, IL-6SV may be used to treat and prevent hemorraghing caused by bone marrow suppression following cancer therapy. Moreover, malignancies involving diverse cell lineages can be treated with the IL-6SV of the present invention.

Immunodeficiency diseases associated with B cell dysfunction, such as common variable immunodeficiency, will respond to IL-6SV administration. Thus, T cell immunodeficiency disorders, particularly involving the T4 subset such as AIDS, may be treated with IL-6SV. IL-6SV may also be used to induce growth in human bone marrow multipotential hemopoietic progenitor cells and promote the differentiation of macrophage/neutrophil bone marrow clones. Thus, IL-6SV may be used for the treatment of conditions of bone marrow dysfunction either congenital or acquired, for example, that acquired in the course of chemotherapy.

IL-6SV may be used to induce liver cells to produce a number of proteins called "acute phase proteins". The acute phase proteins are usually induced after an acute insult, such as traumatic or bacterial shock. Accordingly, administration of IL-6SV during shock may be beneficial in promoting recovery.

IL-6SV may also be used in cell transplant therapy including autogenous bone marrow graft therapy.

IL-6SV may also be employed to enhance erythropoietin production for treating anemias associated with inflammation, renal failure, AIDS, and cancer.

IL-6SV may be used, alone or in combination with other therapeutic products, in the treatment of diseases characterized by a decreased level of either myeloid or lymphoid cells of the hematopoietic system. This protein may also be capable of stimulating accessory and mature cells, e.g., monocytes to produce other hematopoietic-like factors which, in turn stimulate the formation of colonies of other hematopoietic cells, as well as other hematopoietic-like activities.

Various immunodeficiencies, e.g., in T and/or B lymphocytes, or immune disorders, e.g., rheumatoid arthritis, may also be beneficially effected by treatment with IL-6SV. Immunodeficiencies such as leukopenia, a reduction in the number of circulating leukocytes in the peripheral blood, may be the result of viral infections, e.g., HIV, severe exposure to radiation, side effects of cancer therapy or the result of other medical treatment. Therapeutic treatment of leukopenia with IL-6SV compositions may avoid undesirable side effects caused by treatment with presently available drugs. Other conditions susceptible for IL-6SV include patients recovering from bone marrow transplants.

IL-6SV may also be used to augment the humoral or cellular immune response in vivo in co-administration with other therapeutic agents. For example, IL-6SV may be used to enhance the efficacy of viral antigen vaccines, such as HIV or tumor antigen vaccines.

IL-6SV also functions as a hybridomal growth factor in culture medium for hybridoma cell lines to increase the yield thereof.

IL-6SV polypeptides are useful in immunotherapeutic and anti-inflammation compositions. IL-6SV may also be used for the treatment of patients suffering from chemotherapy for bone marrow transfers. IL-6SV may further be utilized to treat corneal damage, keratitis and ulcers.

Among the other treatments IL-6SV may be used for include the reducing conditions, e.g. thrombocytopenia, since IL-6SV promotes mega-karyocyte growth and enhances differentiation into platelet producing cells. IL-6SV may also be used to restore neutrophil and platelet counts in treatment of cancer and in bone marrow transplantation.

This invention provides a method for identification of the receptor for the IL-6SV polypeptide. The gene encoding the receptor can be identified by expression cloning. Briefly, polyadenylated RNA is prepared from a cell responsive to the IL-6SV polypeptide, and a cDNA library created from this RNA is divided into pools and used to transfect COS cells or other cells that are not responsive to IL-6SV. Transfected cells which are grown on glass slides are exposed to labeled IL-6SV. The IL-6SV polypeptide can be labeled by a variety of means including iodidation or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor. As an alternative approach for receptor identification, labeled IL-6SV can be photoaffinity linked with cell membrane or extract preparations that express the receptor molecule. Cross-linked material is resolved by PAGE and exposed to x-ray film. The labeled complex containing the ligand-receptor can be excised, resolved into peptide fragments, and subjected to protein microsequencing. The amino acid sequence obtained from microsequencing would be used to design a set of generate oligonucleotide probes to screen a cDNA library to identify the gene encoding the putative receptor.

This invention provides a method of screening drugs to identify those which enhance (agonists) or block (antagonists) interaction of IL-6SV to its receptor. As an example, a mammalian cell or membrane preparation expressing the IL-6SV receptor would be incubated with labeled IL-6SV in the presence of drug. The ability of drug to enhance or block this interaction could then be measured. Alternatively, the response of a known second messenger system following interaction of ligand and receptor would be measured compared in the presence or absence of drug. Such second messenger systems include but are not limited to, cAMP guanylate cyclase, ion channels or phosphoinositide hydrolysis.

The IL-6SV polypeptides of the present invention may also be employed in accordance with the present invention by expression of such polypeptides in vivo, which is often referred to as "gene therapy." For example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The amounts and dosage regimens of IL-6SV and administered to a subject will depend on a number of factors such as the mode of administration, the nature of the condition being treated and the judgment of the prescribing physician. Generally speaking, they are given, for example, in therapeutically effective doses of at least about 10 µg/kg body weight and in most cases they will be administered in an amount not in excess of about 8 mg/Kg body weight per day and preferably the dosage is from about 10 mg/kg to about 1 mg/kg body weight daily, taking into account the routes of administration, symptoms, etc.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is good, 4,000 is better, and more than 4,000 is probably not necessary to get good results a reasonable percentage of the time.

For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The present invention is also directed to antagonist/inhibitors of the polypeptides of the present invention. The antagonist/inhibitors are those which inhibit or eliminate the function of the polypeptide.

In animals with tumors, elevated levels of circulating IL-6 have been detected. In addition, increased levels of IL-6 have been shown in cancer patients treated with TNF or IL-2. Up regulated production of IL-6 has also been implicated in the pathogenesis of several human diseases, including Castleman's disease, multiple myeloma, cardiac myxoma, cervical cancer, rheumatoid arthritis and autoimmune diabetes.

Antagonists bind to a polypeptide of the present invention and eliminate its function. The antagonist, for example, could be an antibody against the polypeptide which binds to the polypeptide or, in some cases, an oligonucleotide. An antagonists is also a protein which is similar to IL-6SV in all respects but it has no activity such that it recognizes and binds to IL-6SV receptors thereby blocking the receptors. An example of such an antagonist is IL-6SV wherein the active site has been truncated.

An example of an inhibitor is an antisense construct. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of IL-6SV. The antisense RNA oligonucleotide hybridizes to the mRNA in vivo and blocks translation of the mRNA molecule into the IL-6SV polypeptide (antisense—Okano, J. Neurochem., 56:560 (1991); Oligodeoxynucleotides as Antisense Inhibitors of Gene Expression, CRC Press, Boca Raton, Fla. (1988)).

In these ways, the antagonist/inhibitors may be used to treat auto-immune, immunoinflammatory, neoplastic and infectious diseases including multiple myeloma and Kaposi's sarcoma. Inhibition of IL-6SV is also important for treating Castleman's disease, multiple myeloma, cardiac myxoma, cervical cancer, rheumatoid arthritis and autoimmune diabetes. The antagonist/inhibitors may also be used to treat sepsis. The antagonist/inhibitors may be employed in a composition with a pharmaceutically acceptable carrier, e.g., as hereinabove described.

The present invention also relates to an assay for identifying potential antagonist/inhibitors specific to IL-6SV. An example of such an assay combines IL-6SV and a potential antagonist/inhibitor with membrane-bound IL-6SV receptors or recombinant IL-6SV receptors under appropriate conditions for a competitive inhibition assay. IL-6SV can be labeled, such as by radioactivity, such that the number of IL-6SV molecules bound to the receptor can determine the effectiveness of the potential antagonist/inhibitor.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of IL-6SV

The DNA sequence encoding for IL-6SV, ATCC # 75697, is initially amplified using PCR oligonucleotide primers corresponding to the 5' and 3' sequences of the processed IL-6SV protein (minus the signal peptide sequence) and the vector sequences 3' to the IL-6SV gene. Additional nucleotides corresponding to IL-6SV were added to the 5' and 3' sequences respectively. The 5' oligonucleotide primer has the sequence 5'-CGC CAG CCA TGG TAC CCC CAG GAG AAG ATT CCA AAG ATG TAG CCG CCC CAC -3' (SEQ ID NO: 3) contains a Nco I restriction enzyme site followed by 15 nucleotides of IL-6SV coding sequence starting from the presumed terminal amino acid of the processed protein codon. The 3' sequence 3'- GTA GGA AGA TCT CAT TTG CCG AAG AGC -5' (SEQ ID NO: 4) contains complementary sequences to Bgl II restriction site and 15 nucleotides of IL-6SV protein and to a vector sequence located 3' to the IL-6SV DNA insert. The restriction enzyme sites correspond to the restriction enzyme sites on the bacterial expression vector pQE-60. (Qiagen, Inc. 9259 Eton Avenue, Chatsworth, Calif., 91311). pQE-60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-60 was then digested with NcoI and Bgl II. The amplified sequences were ligated into pQE-60 and were inserted in frame with the sequence encoding for the histidine tag and the RBS. The ligation mixture was then used to transform E. coli strain available from Qiagen under the trademark M15/rep 4 by the procedure described in Sambrook J., et al., Molecular Cloning, A Laboratory Manual, Cold Spring Laboratory Press (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized IL-6SV was purified from this solution by chromatography on a Nickel-Chelate column under conditions that allow for tight binding by proteins containing the 6-His tag. Hochuli, E. et al., J. Chromatography 411:177–184 (1984). IL-6SV (95% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

Numerous modifications and variations of the present invention are possible in light of the above teachings and, therefore, within the scope of the appended claims, the invention may be practiced otherwise than as particularly described.

What is claimed is:

1. An isolated polynucleotide comprising:
    a polynucleotide sequence which is at least 95% identical to the sequence of a polynucleotide selected from the group consisting of:
    (a) the polynucleotide encoding a polypeptide comprising an amino acid sequence as set forth in SEQ ID NO:2; and
    (b) the complement of (a).

2. The isolated polynucleotide of claim 1 wherein said polynucleotide sequence is identical to the polynucleotide sequence of (a).

3. The isolated polynucleotide of claim 2 wherein said polynucleotide is a polynucleotide comprising from nucleotide 1 to nucleotide 507 as set forth in SEQ ID NO:1.

4. The isolated polynucleotide of claim 2 wherein the polynucleotide is DNA.

5. The isolated polynucleotide of claim 2 wherein the polynucleotide is RNA.

6. The isolated polynucleotide of claim 1 wherein said polynucleotide is (a).

7. An isolated polynucleotide comprising:
    a polynucleotide sequence which is at least 95% identical to the sequence of a polynucleotide selected from the group consisting of:
    (a) a polynucleotide encoding mature IL-6SV expressed by the DNA contained in ATCC Deposit No. 75697; and
    (b) the complement of (a).

8. The isolated polynucleotide of claim 7 wherein said polynucleotide sequence is identical to (a).

9. The isolated polynucleotide of claim 7 wherein said isolated polynucleotide comprises the DNA contained in ATCC Deposit No. 75697 which encodes and expresses mature IL-6SV.

10. The isolated polynucleotide of claim 6 wherein said polynucleotide is (a).

11. An expression vector comprising the polynucleotide of claim 2.

12. An expression vector comprising the polynucleotide of claim 3.

13. An expression vector comprising the polynucleotide of claim 4.

14. An expression vector comprising the polynucleotide of claim 6.

15. An expression vector comprising the polynucleotide of claim 8.

16. An expression vector comprising the polynucleotide of claim 9.

17. An expression vector comprising the polynucleotide of claim 10.

18. Host cell transfected with the vector of claim 11.
19. Host cell transfected with the vector of claim 12.
20. Host cell transfected with the vector of claim 13.
21. Host cell transfected with the vector of claim 14.
22. Host cell transfected with the vector of claim 15.
23. Host cell transfected with the vector of claim 16.
24. Host cell transfected with the vector of claim 17.

25. A process for producing a polypeptide comprising:
    culturing the host cell of claim 18 under conditions suitable to produce the polypeptide encoded by said polynucleotide; and recovering said polypeptide.

26. A process for producing a polypeptide comprising:

culturing the host cell of claim 19 under conditions suitable to produce the polypeptide encoded by said polynucleotide; and recovering said polypeptide.

27. A process for producing a polypeptide comprising:

culturing the host cell of claim 20 under conditions suitable to produce the polypeptide encoded by said polynucleotide; and recovering said polypeptide.

28. A process for producing a polypeptide comprising:

culturing the host cell of claim 21 under conditions suitable to produce the polypeptide encoded by said polynucleotide; and recovering said polypeptide.

29. A process for producing a polypeptide comprising:

culturing the host cell of claim 22 under conditions suitable to produce the polypeptide encoded by said polynucleotide; and recovering said polypeptide.

30. A process for producing a polypeptide comprising:

culturing the host cell of claim 23 under conditions suitable to produce the polypeptide encoded by said polynucleotide; and recovering said polypeptide.

31. A process for producing a polypeptide comprising:

culturing the host cell of claim 24 under conditions suitable to produce the polypeptide encoded by said polynucleotide; and recovering said polypeptide.

32. An isolated polynucleotide comprising a polynucleotide selected from the group consisting of a polynucleotide encoding the mature interleukin-6 splice variant protein of SEQ ID NO:2 and a naturally occurring allelic variant thereof.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 507 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
GCCCCAGTAC  CCCCAGGAGA  AGATTCCAAA  GATGTAGCCG  CCCCACACAG  ACAGCCACTC   60
ACCTCTTCAG  AACGAATTGA  CAAACAAATT  CGGTACATCC  TCGACGGCAT  CTCAGCCCTG  120
AGAAAGGAGA  CATGTAACAA  GAGTAACATG  TGTGAAAAAG  ATGGATGCTT  CCAATCTGGA  180
TTCAATGAGG  AGACTTGCCT  GGTGAAAATC  ATCACTGGTC  TTTTGGAGTT  TGAGGTATAC  240
CTAGAGTACC  TCCAGAACAG  ATTTGAGAGT  AGTGAGGAAC  AAGCCAGAGC  TGTGCAGATG  300
AGTACAAAAG  TCCTGATCCA  GTTCCTGCAG  AAAAAGGCAA  AGAATCTAGA  TGCAATAACC  360
ACCCCTGACC  CAACCACAAA  TGCCAGCCTG  CTGACGAAGC  TGCAGGCACA  GAACCAGTGG  420
CTGCAGGACA  TGACAACTCA  TCTCATTCTG  CGCAGCTTTA  AGGAGTTCCT  GCAGTCCAGC  480
CTGAGGGCTC  TTCGGCAAAT  GTAGCAT                                        507
```

( 2 ) INFORMATION FOR SEQ ID NO:2:

( i ) SEQUENCE CHARACTERISTICS:
        ( A ) LENGTH: 167 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Ala  Pro  Val  Pro  Pro  Gly  Glu  Asp  Ser  Lys  Asp  Val  Ala  Ala  Pro
               5                        10                       15

His  Arg  Gln  Pro  Leu  Thr  Ser  Ser  Glu  Arg  Ile  Asp  Lys  Gln  Ile
              20                        25                       30

Arg  Tyr  Ile  Leu  Asp  Gly  Ile  Ser  Ala  Leu  Arg  Lys  Glu  Thr  Cys
              35                        40                       45

Asn  Lys  Ser  Asn  Met  Cys  Glu  Lys  Asp  Gly  Cys  Phe  Gln  Ser  Gly
              50                        55                       60

Phe  Asn  Glu  Glu  Thr  Cys  Leu  Val  Lys  Ile  Ile  Thr  Gly  Leu  Leu
              65                        70                       75

Glu  Phe  Glu  Val  Tyr  Leu  Glu  Tyr  Leu  Gln  Asn  Arg  Phe  Glu  Ser
              80                        85                       90

Ser  Glu  Glu  Gln  Ala  Arg  Ala  Val  Gln  Met  Ser  Thr  Lys  Val  Leu
              95                       100                      105

Ile  Gln  Phe  Leu  Gln  Lys  Lys  Ala  Lys  Asn  Leu  Asp  Ala  Ile  Thr
             110                       115                      120

Thr  Pro  Asp  Pro  Thr  Thr  Asn  Ala  Ser  Leu  Leu  Thr  Lys  Leu  Gln
             125                       130                      135

Ala  Gln  Asn  Gln  Trp  Leu  Gln  Asp  Met  Thr  Thr  His  Leu  Ile  Leu
             140                       145                      150

Arg  Ser  Phe  Lys  Glu  Phe  Leu  Gln  Ser  Ser  Leu  Arg  Ala  Leu  Arg
             155                       160                      165

Gln  Met
```

( 2 ) INFORMATION FOR SEQ ID NO:3:

( i ) SEQUENCE CHARACTERISTICS:
        ( A ) LENGTH: 51 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

```
CGCCAGCCAT GGTACCCCCA GGAGAAGATT CCAAAGATGT AGCCGCCCCA C   51
```

( 2 ) INFORMATION FOR SEQ ID NO:4:

( i ) SEQUENCE CHARACTERISTICS:
        ( A ) LENGTH: 27 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

```
GTAGGAAGAT CTCATTTGCC GAAGAGC                               27
```

( 2 ) INFORMATION FOR SEQ ID NO:5:

( i ) SEQUENCE CHARACTERISTICS:
        ( A ) LENGTH: 185 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:5:

-continued

| | | | | | | | | | | | | | | |
|---|---|---|---|---|---|---|---|---|---|---|---|---|---|---|
| Ala | Pro | Val | Pro | Pro 5 | Gly | Glu | Asp | Ser | Lys 10 | Asp | Val | Ala | Ala | Pro 15 |
| His | Arg | Gln | Pro | Leu 20 | Thr | Ser | Ser | Glu | Arg 25 | Ile | Asp | Lys | Gln | Ile 30 |
| Arg | Tyr | Ile | Leu | Asp 35 | Gly | Ile | Ser | Ala | Leu 40 | Arg | Lys | Glu | Thr | Cys 45 |
| Asn | Lys | Ser | Asn | Met 50 | Cys | Glu | Ser | Ser | Lys 55 | Glu | Ala | Leu | Ala | Glu 60 |
| Asn | Asn | Leu | Asn | Leu 65 | Pro | Lys | Met | Ala | Glu 70 | Lys | Asp | Gly | Cys | Phe 75 |
| Gln | Ser | Gly | Phe | Asn 80 | Glu | Glu | Thr | Cys | Leu 85 | Val | Lys | Ile | Ile | Thr 90 |
| Gly | Leu | Leu | Glu | Phe 95 | Glu | Val | Tyr | Leu | Glu 100 | Tyr | Leu | Gln | Asn | Arg 105 |
| Phe | Glu | Ser | Ser | Glu 110 | Glu | Gln | Ala | Arg | Ala 115 | Val | Gln | Met | Ser | Thr 120 |
| Lys | Val | Leu | Ile | Gln 125 | Phe | Leu | Gln | Lys | Lys 130 | Ala | Lys | Asn | Leu | Asp 135 |
| Ala | Ile | Thr | Thr | Pro 140 | Asp | Pro | Thr | Thr | Asn 145 | Ala | Ser | Leu | Leu | Thr 150 |
| Lys | Leu | Gln | Ala | Gln 155 | Asn | Gln | Trp | Leu | Gln 160 | Asp | Met | Thr | Thr | His 165 |
| Leu | Ile | Leu | Arg | Ser 170 | Phe | Lys | Glu | Phe | Leu 175 | Gln | Ser | Ser | Leu | Arg 180 |
| Ala | Leu | Arg | Gln | Met 185 | | | | | | | | | | |